United States Patent [19]

Neeley

[11] Patent Number: 5,401,110
[45] Date of Patent: Mar. 28, 1995

[54] CUSTOM LABEL PRINTER

[76] Inventor: William E. Neeley, 22 High View Rd., Madison, Conn. 06443

[21] Appl. No.: 729,691

[22] Filed: Jul. 15, 1991

[51] Int. Cl.6 .............................................. B41J 11/26
[52] U.S. Cl. ..................................... 400/621; 235/375
[58] Field of Search .................. 400/61, 621, 611, 120, 400/73, 691; 235/375; 40/310

[56] References Cited

U.S. PATENT DOCUMENTS

| | | | |
|---|---|---|---|
| 4,734,713 | 3/1988 | Sato | 346/76 PH |
| 4,830,522 | 5/1989 | Sato | 400/120 |
| 4,857,713 | 8/1989 | Brown | 235/375 |
| 4,857,716 | 8/1989 | Gombrich | 235/462 |
| 4,930,263 | 7/1990 | Rando | 51/165.71 |
| 4,976,351 | 12/1990 | Mangini | 206/232 |
| 4,988,221 | 1/1991 | Shibayama | 400/61 |
| 5,051,565 | 9/1991 | Wolfram | 235/384 |
| 5,061,947 | 10/1991 | Morrison | 346/1.1 |
| 5,092,688 | 3/1992 | Haennelt | 400/120 |

FOREIGN PATENT DOCUMENTS 110480  7/1982  Japan .................... 400/621

OTHER PUBLICATIONS

IBM Technical Disclosure Bulletin, vol. 26, No. 4, Sep. 1983 "Serial Printer Paper Guillotine", R. H. Harris, pp. 2089–2090.
IBM Technical Disclosure Bulletin, vol. 26, No. 8, Jan. 1984 "Compact Paper Guillotine", Colby et al., pp. 4191–4192.

Primary Examiner—Edgar S. Burr
Assistant Examiner—Ren Yan
Attorney, Agent, or Firm—William W. Jones

[57] ABSTRACT

The label printer uses a continuous strip of label paper on which customized size labels are printed. The printer is operated by a microprocessor into which label criteria, such as size, print content, type, and the like are inputted. Specimen tubes having machine readable labels on them are scanned by a scanner connected to the microprocessor so as to identify the respective sizes of the specimen tubes, and type of label desired. The printer has a label paper strip perforator which is controlled by the microprocessor so as to produce properly sized labels for affixation to the specimen tubes. The printed labels can be used for different lab labeling requirements such as slides or other tubes for aliquots of the original specimen sample.

9 Claims, 5 Drawing Sheets

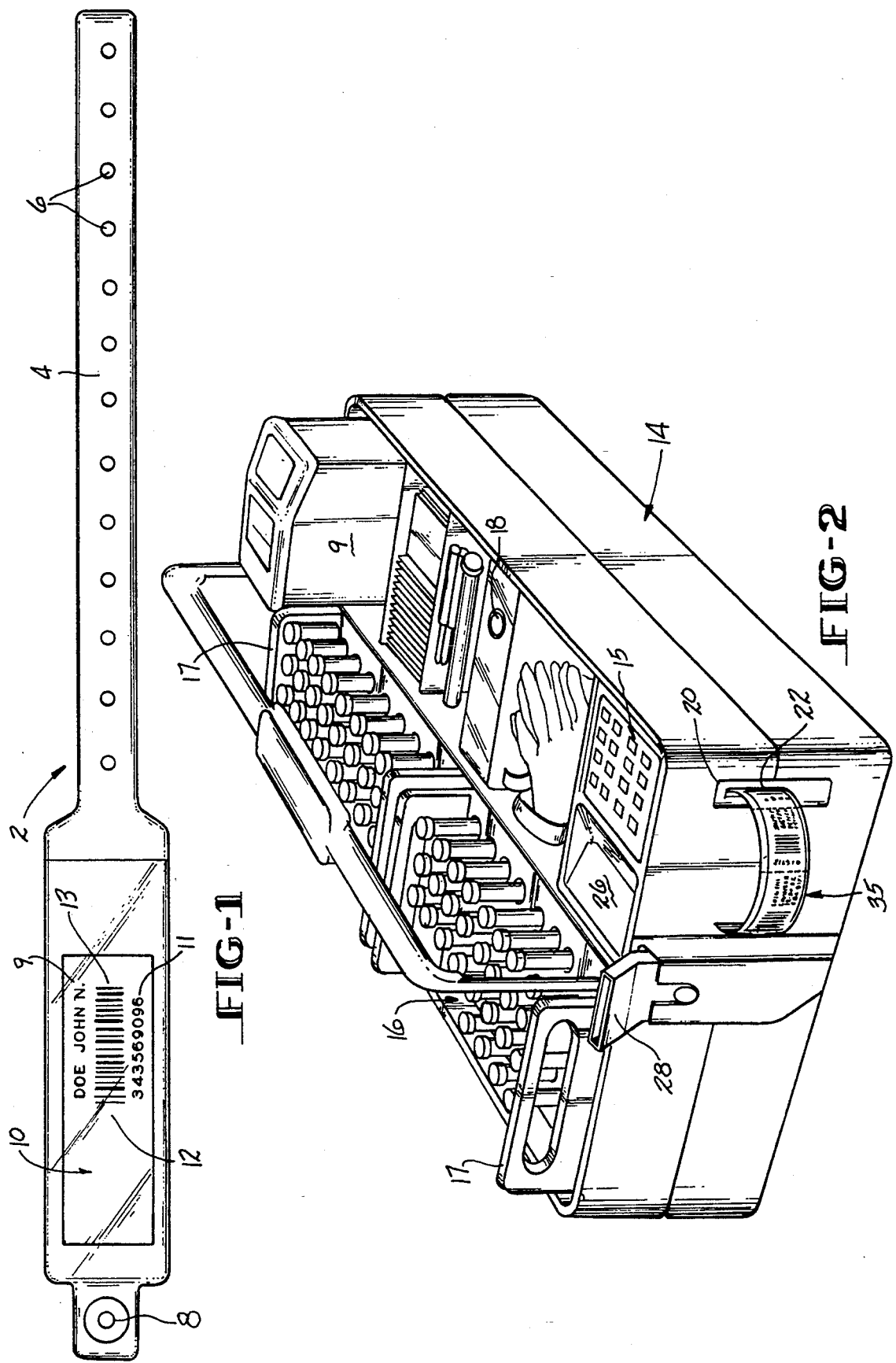

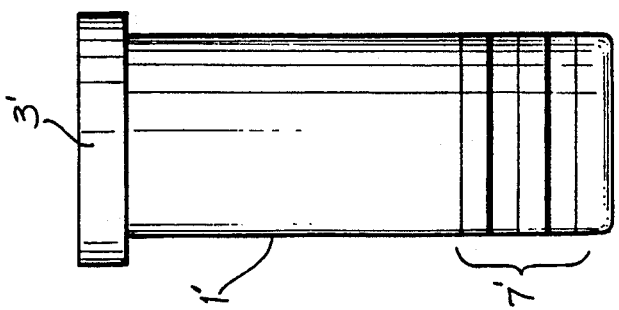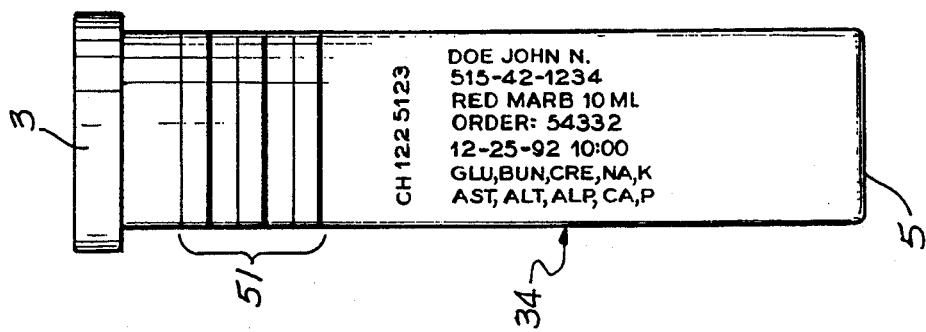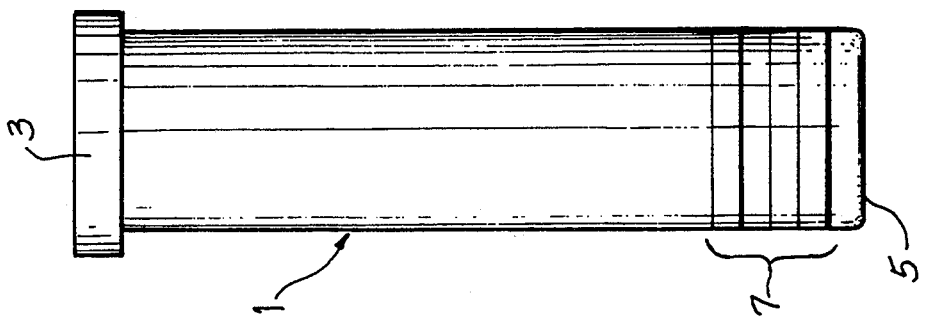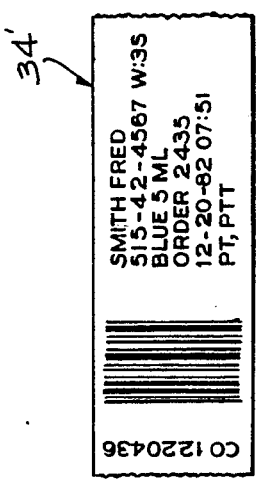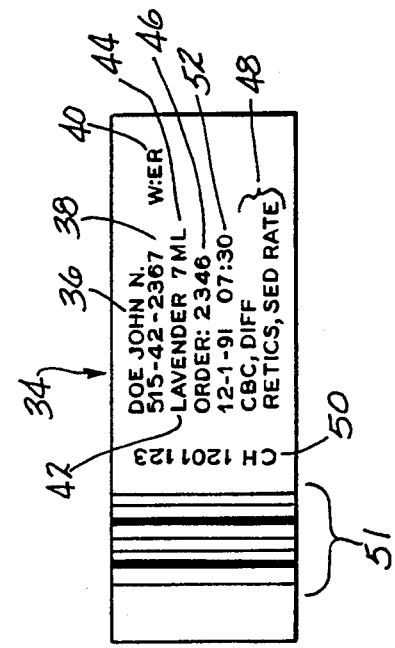

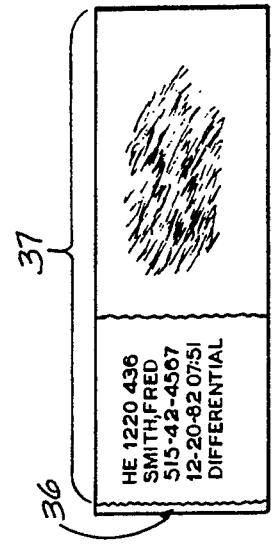
FIG-12
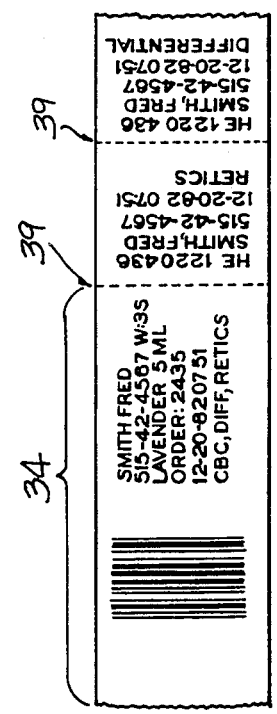
FIG-10
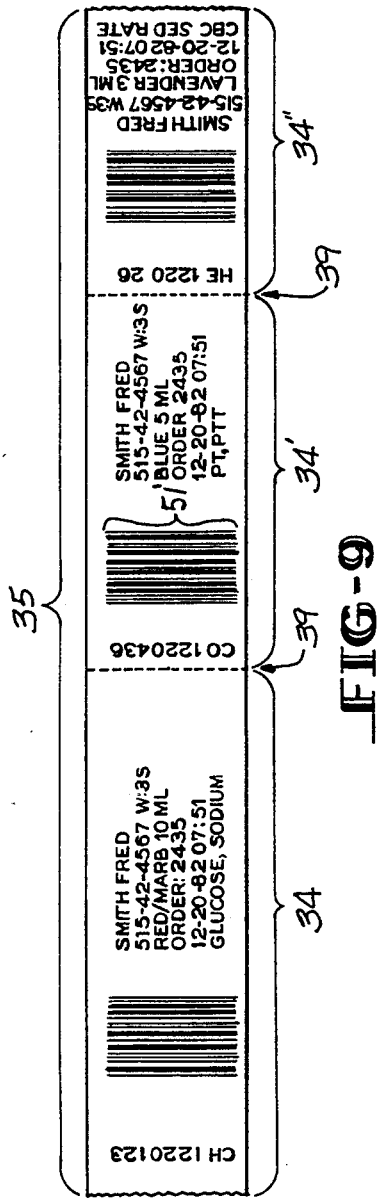
FIG-9
FIG-8
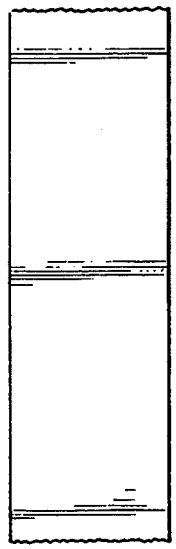
FIG-11
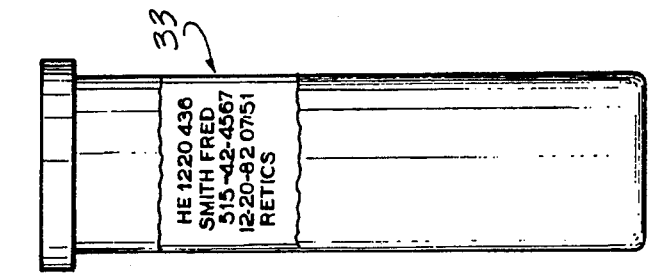

CUSTOM LABEL PRINTER

FIELD OF THE INVENTION

This invention relates to an improvement in label printers and procedures, whereby labels can be produced for attachment to medical specimen tubes, which labels will be custom sized, and configured for different specimen tubes. More particularly, this invention relates to a printer and procedure wherein the customized labels are produced at the patient' bedside when the specimen samples are taken.

DESCRIPTION OF RELATED ART

Current hospital patient specimen gathering procedures involve the use of specimen sample tubes of different sizes in which a specimen sample drawer will place the specimens. As noted, the specimen tubes will be of different sizes, for example: 12 ml; 10 ml; 7 ml; 5 ml; and the like. The specimen tubes will be prelabeled in the lab in some cases, prior to sampling rounds, and in other cases, the tubes will have to be labeled when the specimens are drawn, especially in an emergency room or intensive care setting. In the former case, the different sized tubes can be provided with preprinted labels which match the tube sizes. In the latter case, the labels will be taken from a supply of blank labels which will generally be all the same size; and the patient and specimen test information will have to be manually printed on the labels.

The prior patent art contains teachings for use in the hospital environment relating to the dispensing of medications and the gathering of specimen samples which are intended to reduce the risk of human error in these prior art procedures, the patient will be provided with a wristband which has machine readable indicia, such as a bar code, which identifies the patient, which bar code is printed thereon and which bar code is to be read by a portable scanner carried by the hospital personnel. Preprinted labels are provided which also have a patient-specific bar code printed thereon. The bar codes on the labels are different from the bar codes on the wristband, but both bar codes identify the same patient. The preprinted labels are disposed on a patient list, and when the hospital attendent scans the patient's wristband, a subsequent scan of all of the labels is necessary until a match is found. Since the labels are all preprinted, they can be sized to match the size of the tubes to which they are to be affixed. There is some discussion of printing labels at the bedside in the prior art, but there is no discussion of matching label size to tube size, or of producing otherwise customized labels at the bedside. The aforesaid teachings are contained in U.S. Pat. Nos. 4,628,193 granted Dec. 9, 1986 to A. S. Blum; and 4,835,372 granted May 30, 1989 to P. P. Gombrich et al.

Copending U.S. patent application Serial No. 410,144, filed Sep. 20, 1989 by W. E. Neeley discloses a procedure and assembly for drawing blood which involves the use of a portable instrument, as for example a specimen sampling tube tray, which has an onboard microprocessor which stores and uses information from the main hospital computer. An onboard label printer is also included in the instrument. The microprocessor is connected to and operates the printer. A bar code scanner is also mounted in the instrument and connected to the microprocessor. The scanner is used to scan a patient's wrist band at bedside. The scanned bar code tells the microprocessor who the patient is, and the microprocessor causes the printer to print a label at the bedside. The label will include the patient's printed accession number in bar code and alphanumeric form, and the patient's name, specimen testing instructions, and the time and date the specimen is drawn; the latter all being printed in human readable alphanumeric indicia. This application does not address the problems which arise from bedside label production for specimen tubes, which tubes are different sizes. The use of a 12 ml tube label on a 5 ml tube is obviously inappropriate, but is tolerated when a stock of common sized labels are used with a printer that dispenses labels from one strip roll.

Copending U.S. patent application Ser. No. 689,476 filed Apr. 23, 1991 by William E. Neeley et al describes a procedure for drawing blood samples which involves an automatic identification of tube type and size at bedside, along with patient identification and test instructions. This procedure also does not speak to the problem of producing customized labels for different tube sizes, or labels customized for different lab labeling requirements.

In the prior art, the production of medical specimen labels, whether preprinted, or printed at bedside, are printed on a label strip roll which incudes a waxed or other non-stick paper type backing sheet and individual adhesive coated labels which are carried on the backing sheet. The labels on any specific label strip roll are all the same size, and are all the same type, whereby one label strip roll cannot be used to produce labels which are different in size or type. Once the labels are printed, they are peeled off of the backing sheet and applied to the tubes. Obviously, when different sized tubes are being prelabeled, a number of different label strip rolls must be used. When different size labels are being printed at bedside from a single label strip roll, then all of the labels will be the same size, irrespective of the size of the tubes to which they are to be affixed.

Beyond the problem of label size, there are also occasions where different types of specimen labels will be called for. On these occasions, the labels must be preprepared, since there are no provisions in the prior art where different label types can be created at the patient's bedside. An example of such a customized label type is where a label has a first portion which will be adhered to the specimen tube, and also includes one or more second detachable label portions which are carried to the lab by the first label portion on the tube, and which second label portions are then separated from the first portion for adhering to one or more specimen slides. The first label portion and the subsequent label portions should both be printed with patient identification information and specimen testing instructions thereon, along with specimen-drawing time information. Tube type and tube size information may also be printed on all portions of the label. To date, the prior art has not suggested any procedure for producing such customized labels from a single label strip roll.

SUMMARY OF THE INVENTION

This invention relates to a procedure and apparatus for producing customized medical specimen labels at the bedside of a patient when the specimen samples are taken from the patient. The apparatus is preferably a specimen tube tray which is portable and which is carried by the hospital technician on specimen gathering rounds. The technician is provided with a supply of different size tubes which are adapted with reagents and the like for performing different blood tests on blood samples drawn into the tubes. The sample tubes have preaffixed machine readable labels thereon which can be scanned by a scanner on the tray so as to identify the size of the tube and the tests for which it has been adapted. The tray is provided with a microprocessor connected to the scanner. The microprocessor has inputted therein information as to label size and content, as well as customized characteristics, which information is correlated to the machine readable indicia on the preaffixed specimen tube labels. Once a scan of a specimen tube is made, the microprocessor knows what kind and size tube is going to be used, and knows what specimen testing information should be printed on the label. The patient will be provided with a wristband, or chart label which also has machine readable indicia thereon which will be scanned by a scanner on the tray to inform the microprocessor of the identity of the patient. Once both the specimen tube and the wristband have been scanned, the microprocessor knows: who the patient is; what size tube is being used; what tests are to be performed; whether a special label (I.e. with removable slide tabs) is required; and any other peculiarities of the label which is to be attached to the specimen tube into which the current sample is being drawn.

The tray or the like also includes a specimen tube label printer which is controlled by the microprocessor. The printer prints the scanned programmed patient and testing information onto the labels, and also includes a label strip drive and coordinated label strip perforator which is operated by the microprocessor to form properly sized labels, and also to form customized labels as needed, which customized labels may include detachable slide tabs, or the like. Once the tube is scanned, the microprocessor can cause the printer and perforator to prepare a label which label has the required size, and has any required auxiliary physical features. Thus, the device can provide fully customized labels at the patient's bedside which are appropriately sized and configured for the specimen tubes and tests to be performed.

It is therefore an object of this invention to provide an improved procedure for taking and labeling patient samples in a hospital, or the like, environment.

It is a further object of this invention to provide an improved procedure of the character described which eliminates the chances of producing improper labels for specimen tubes.

It is an additional object of this invention to provide an improved procedure of the character described wherein customized specimen tube labels are printed at the time of taking the specimens.

It is another object of this invention to provide an improved procedure of the character described wherein specimen tube labels displaying patient identification, and test instruction information, and customizedly sized and configured, are produced by scanning machine-readable indicia on a patient's hospital ID wrist band, and also scanning machine readable indicia on the specimen tube, thereby triggering a bedside microprocessor to print a customized specimen tube label at the patient's bedside.

These and other objects and advantages of the invention will become more readily apparent from the following detailed description of a preferred embodiment thereof when taken in conjunction with the accompanying drawings in which:

DESCRIPTION OF DRAWINGS

FIG. 1 is a plan view of a hospital patient identification bracelet adapted for use in practicing this invention;

FIG. 2 is a perspective view of a blood specimen tube microprocessor-printer-scanner tray assembly employing this invention;

FIG. 3 is a side elevational view of an evacuated specimen tube which has disposed thereon machine readable coded indicia which identifies the type of, and size of the tube, i.e., a specimen tube ID label;

FIG. 4 is a plan view of a patient and specimen test instruction label for a lavender stopper for affixation to the tube, which label is printed at bedside by the device of this invention.

FIG. 5 is a view similar to FIG. 3, but showing a printed patient and specimen test instruction label for a red marble stopper affixed thereto adjacent to the specimen tube ID label;

FIG. 6 is a view similar to FIG. 3, but showing a smaller volume specimen tube;

FIG. 7 is a view similar to FIG. 4, but showing a label adapted to be attached to the specimen tube of FIG. 6;

FIG. 8 is a plan view of a label strip suitable for use in connection with this invention;

FIG. 9 is a plan view of a label strip similar to FIG. 8, but showing the strip perforated by the printer/perforator so as to provide different size labels for attachment to different size tubes;

FIG. 10 is a plan view of a label strip similar to FIG. 8, but showing the strip perforated by the printer/perforator so as to provide a sequence of customized labels which include tear-off specimen tube or slide labels;

FIG. 11 is a side elevational view of a specimen tube having one of the labels of FIG. 10 affixed thereto;

FIG. 12 is a plan view of a blood smear specimen slide having customized slide label affixed thereto;

SPECIFIC EMBODIMENT

Figure 13:
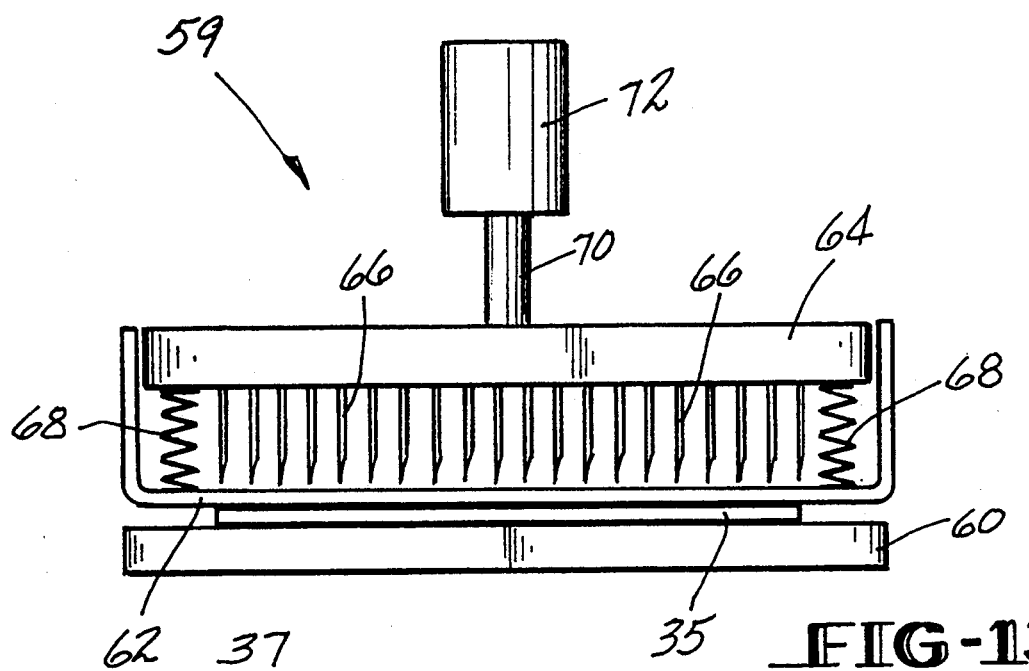
FIG. 13 is a somewhat schematic cross sectional view of the label printer showing the label perforator in its retracted position.

Referring now to FIG. I, there is shown a conventional hospital patient ID bracelet 2 which includes a strap portion 4 having serial apertures 6 for receiving a snap fastener 8 on the end of the bracelet 2. A pocket pouch 10 on the bracelet receives a patient identification slip or tag 12 having the patient's name 9 printed on it, and having the patient's hospital identification number printed on it, both in alphanumeric form 11, and also in a machine-readable form such as a bar code 13. All of the patient's records in the hospital will be in part catalogued and identified by this patient hospital identification number.

Referring to FIG. 2, there are shown details of a blood sampling tray which has been adapted to operate in accordance with this invention. The tray 14 includes a portion 16 thereof which is adapted to receive a plurality of specimen sampling tube racks 17 therein. A needle discard receptacle 9 is included in the tray 14. A specimen tube label printer 20 is built into the tray 14.

The printed specimen tube labels are ejected from the printer 20 via slot 22. It will be understood that the label printer 20 is preloaded with a roll of blank label strip 35 which is precoated with an adhesive and adhered to a non-bonding strip of material, such as waxed paper, or the like. Finished labels thus can be readily peeled from the waxed paper strip. The printer 20 is controlled by a microprocessor housed in the tray 14. The tray has a liquid crystal display 26 which will specify to the specimen drawer the numbers and types of specimen tubes, which are to be used to take specimens from the patient after the wrist band has been scanned.

The tray 14 also has a keyboard 15 which is linked to the microprocessor. The keyboard 15 can be used for many functions, one of which is to allow a patient specimen test instruction label to be printed for use on a specimen tube which is either a size other than that specified or a specimen tube which has no tube identification number preprinted thereon. These changes would require a manual override by the drawer. The need to use such an override could arise were the drawer to run out of a certain type, or size, tube before the necessary specimens had all been drawn. For example: if all of the 5 mL prelabeled red stoppered tubes had been used before all of the 5 mL specimens had been drawn, the drawer could draw the specimen in a prelabeled 7 mL, or 10 mL, red stoppered tube by keying a pre-identified override code into the microprocessor with the keyboard, and then scanning the 7 mL red stoppered tube to produce a patient identification label from the printer. If only non-labeled 5 mL red stoppered tubes are available, then a more complicated series of pre-identified override codes could be keyed in by the drawer, to allow a patient identification label to be printed. In this manner, the drawer cannot accidentally draw and label a patient specimen in a nonlabeled tube. Labeling the specimen in such a tube or in an improper sized tube can only be done by the drawer intentionally, by overriding the microprocessor lockout with the keyboard, to permit the onboard printer to print a patient and specimen test instruction label despite the use of a non-recognized tube.

The keyboard can also be used by the drawer to input instructions to the microprocessor to reprint a previously printed label. This option is useful when the drawer will have affixed a bedside printed specimen label to one of the evacuated tubes, and then been unable to properly draw the blood sample for failure to find a vein, whereupon the vacuum in the tube has been lost. In such a case the labeled empty tube must be discarded whereby the label is effectively lost. It is practically impossible to remove an adhered label from one tube and then re-adhere it to another tube. In such a case, a reprint key on the keyboard may be pressed and a replacement tube scannned to obtain a second label identical to the lost label.

A hand held bar code scanner 28 is operably connected to the tray microprocessor. The scanner 28 is preferably a laser or charge-coupled device scanner which is adapted to read the patient's ID bracelet which, due to the fact that it is worn on an irregular surface, i.e. one's wrist, is difficult for a conventional wand scanner to read.

Referring to FIG. 3 there is shown a specimen tube 1 having a stopper 3 of predetermined color and having preprinted tube identification indicia positioned thereon adjacent to the closed end 5 of the tube 1.

FIG. 4 shows a typical specimen tube label 34 produced by the printer 20 after the ID bracelet tag 12 and specimen tube ID label have been scanned. The label 34 displays the patient's name 36; ID number 38; the patient ward location 40; the tube type 42; the specimen volume 44; the patient order number 46; the tests to be performed 48; the patient test accession number in alphanumeric form 50 and in bar code form 51; and the time and date the specimen is drawn 52.

FIG. 5 shows the tube 1 of FIG. 3 after the specimen label 34 has been printed and affixed to the tube at bedside. One edge of the label 34 is positioned so as to abut the stopper 3. This places the bar coded patient accession number 51 in the proper place to be scanned by the automatic laboratory specimen testing equipment contained in modern hospitals. The label 34 is of sufficient length to cover the bar code 7 on the tube 1. This will privent laboratory scanners from sensing the tube bar code 7.

FIG. 6 shows a tube 1' similar to the tube of FIG. 3 but smaller in size. The tube 1' will typically have a stopper 3' which is a different color that the stopper 3, and will also have its own tube and test indentifying indicia 7' which identifies it as a tube that is different from the tube 1.

Interfacing both of the scanners 28 and 31 with the microprocessor enables the microprocessor to identify the patient and also the specimen tube type, and thereafter, only when both identifications have been made, enable the printer 20 to print the proper label with: correct patient identification; patient accession number; testing instructions; date and time; and tube ID indicia, for placement on the specimen tube.

FIG. 7 shows a label 34' similar to the label 34, but with different tube and test information on it, so as to be compatable with the specimen tube 1'. It will be noted that the label 34' is smaller than the label 34 since the tube 1' is smaller than the tube 1.

Referring to FIGS. 8–10, label strip 35 which is preferably a continuous strip, has a paper layer 37 on which patient, tube, and specimen testing information is printed. The opposite side of the strip 35 is a protective non-stick backing material which protects an adhesive coating on the back of the paper layer 37. As previously noted, the printer both prints, sizes, and stylizes the finished labels, as illustrated in FIGS. 9 and 10. The printer is able to form transverse perforated lines 39 in the strip 35 so as to form different size labels 34, 34' and 34" for different size tubes. For example, the label 34 can be sized for tubes in the 100 mm range; the label 34' can be sized for tubes in the 65 to 73 mm range; and the label 34" can be sized for tubes in the 47 mm range. All of the necessary information including the tests to be done are printed on the labels as noted in FIG. 9. Smaller fonts are used to allow essential information to be printed on smaller labels. The component label 34' in the compound label 35 has a bar code 51' printed thereon which is specific to an external reference sample testing laboratory such as Smith Kline Beecham, or the like. With such a compound label is printed at bedside, some of the component labels will be placed on specimen carriers which are to be tested inside the hospital and thus will carry one bar code, and other of the component labels will be placed on specimen carriers which are sent to commercial testing laboratories which are outside of the hospital, and thus will carry a bar code which is peculiar to such external labs.

FIG. 10 shows a customized label formed by the printer. The label has a main portion 34 on which full patient, tube size and type, and testing instructions are printed. Transverse scores 39 subdivide the label into main portions 34, and additional satellite labels 33 and 36. The main label portion 34 displays all of the tests to be run on the specimen sample, while each of the additional or supplemental labels contains only the information essential to identify the patient and the procedure to be done. For example, when the original sample arrives in the laboratory processing area, a portion of the sample can be poured into a second test tube and satellite label 33 is attached to provide positive identification. This tube can be taken to one area of the laboratory where a reticulocyte test is done. Satellite label 36 is removed in the processing area and attached to a glass slide on which a drop of the patient's blood is smeared, stained and a differential count of white cells is done. This smaller label provides positive identification of the slide. This is a major improvement in slide identification which is usually done by writing the patient's name on the slide. As an option, (not shown in FIG. 10) a bar code can also be printed on the satellite labels, if desired.

FIG. 11 shows a sample tube 1 having a satellite label 33 of the type shown in FIG. 10 affixed thereto. FIG. 12 shows a satellite label 36 attached to a blood smear slide 37.

Figure 14:
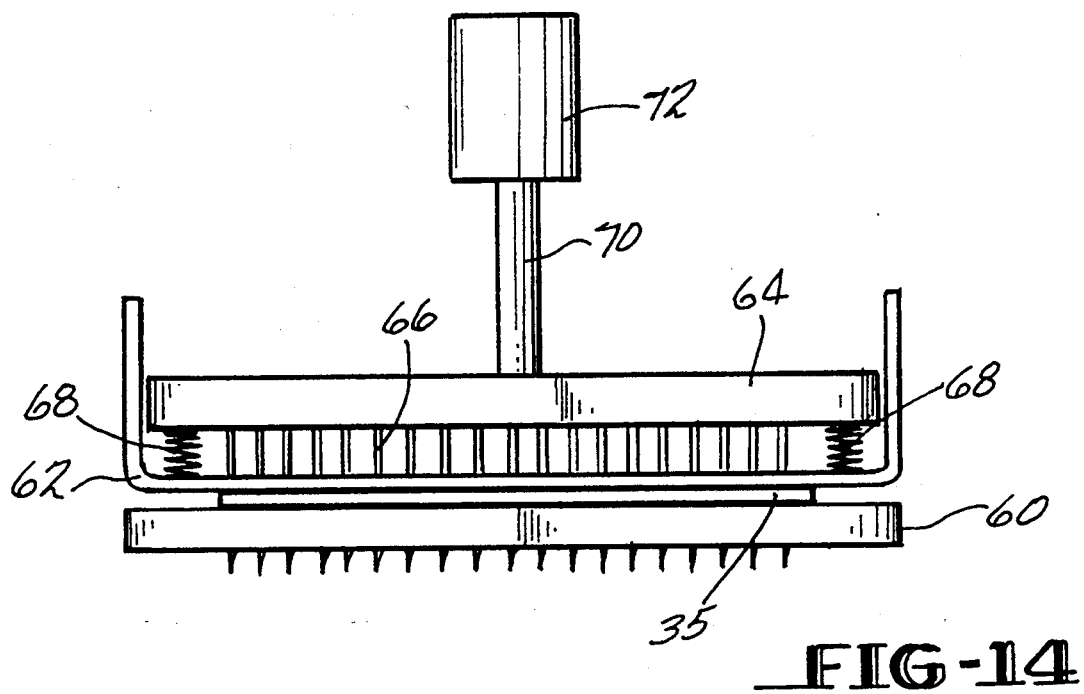
FIG. 14 is a view similar to FIG. 13 but showing the perforator in its cutting position, wherein the label strip is scored.

FIGS. 13 and 14 illustrate the components and mode of operation of the label perforator which is denoted generally by the numeral 59. The perforator is incorporated into the label printer. The label strip 35 is fed across a perforated backing plate 60 and beneath a perforated presser plate 62. A rack 64 is disposed above the presser plate 62, strip 35, and backing plate 60. The rack 64 has a plurality of closely spaced depending tines 66 thereon which are normally spaced upwardly away from the plates 60 and 62, and the strip 35. The rack 64 and tines 66 are biased to their withdrawn position shown in FIG. 12 by a pair of springs 68 sandwiched between the plate 62 and the rack 64. A push rod 70, actuated by a solenoid 72, causes the rack 64 and tines 66 to move to a perforating position to form the perforation score lines on the label strip 35.

FIG. 14 shows the perforator in its operable position wherein the tines 66 are driven through the plates 62 and 60, and through the label strip 35 by actuation of the solenoid 72 and push rod 70.

Figure 15:
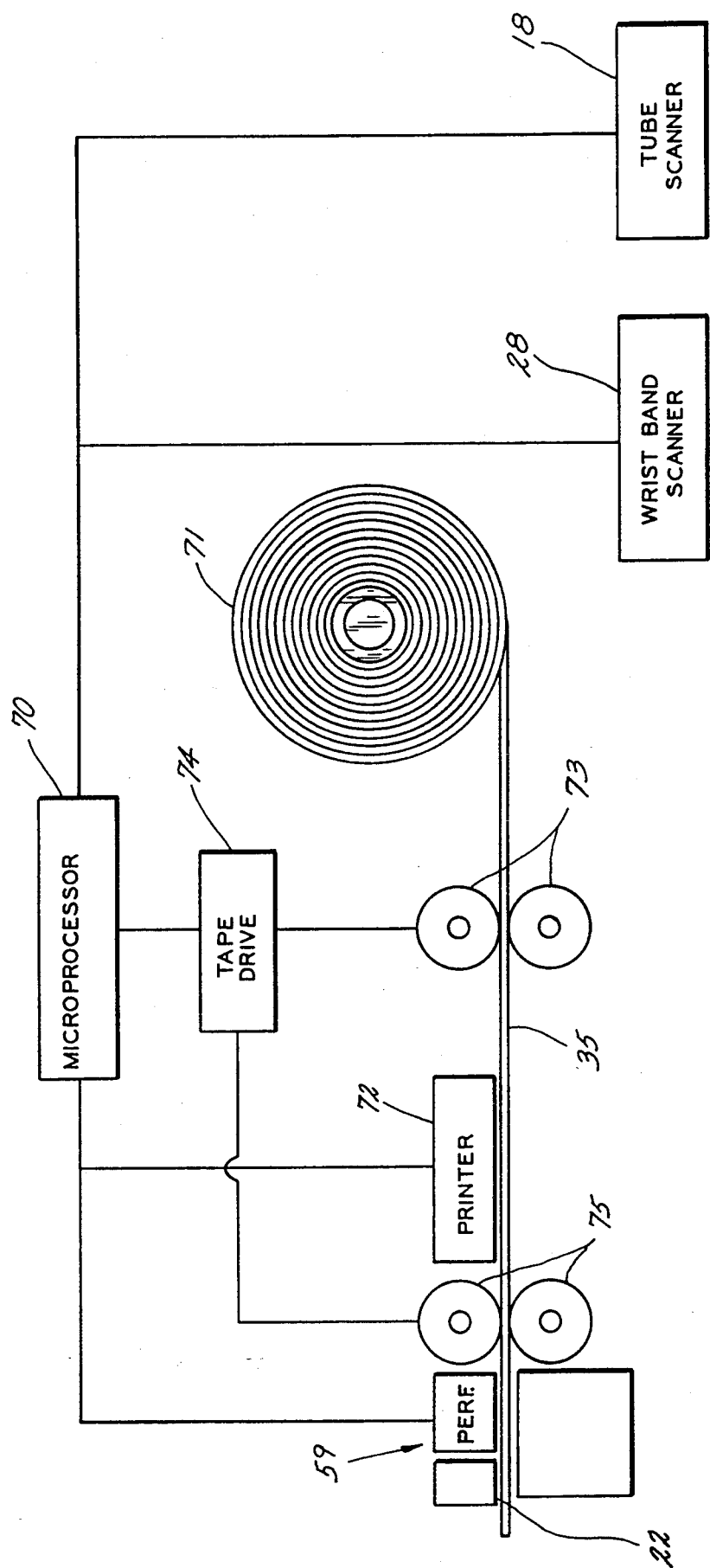
FIG. 15 is a somewhat schematic view of the system label printer/perforator and its connections with the scanner means and the microprocessor.

Referring to FIG. 15, a somewhat schematized view of the label production portion of the device is shown. The label strip 35 is wound on a roll 71 and the strip 35 is fed by, and through, drive rollers 73 and 75. The strip 35 passes through a label printer 72 and through the label perforator 59.

Thereafter, the label strip 3S exits the tray via the tear slot 22. The onboard microprocessor 70 which retains patient information and specimen tube and testing information, is connected to the tube scanner 8 and also to the patient wrist band scanner 28 to receive relevant information from both of the scanners 18 and 28. The microprocessor 70 also operates the printer 72 and the strip perforator 59. Once the tube scanner 18 and the wristband scanner 28 identify the patient; the tube type and size; and the specimen testing instructions for the microprocessor 70, the microprocessor 70 then knows what size tube is being used, and therefore what size label should be printed. Thus it knows what cutting mode to use for the preforator 59. The microprocessor 70 also knows from downloading from the main hospital computer, whether customized labels with slide or other satellite tabs are indicated, and it operates the perforator 59 accordingly. The wristband scanner 28 and the tube scanner 18 also tell the microprocessor 70 what information is to be printed on the labels, thus, the microprocessor 70 knows how to operate the printer 72. The microprocessor, with input from the scanners, is thus able to use the printer and perforator to form customized labels at the patient's bedside. The tube and patient barcode scanning steps can be performed by separate pieces of equipment, or can be performed by an integrated single scanner.

It will be readily appreciated that this invention provides for safer, more accurate, specimen sampling of patients with customized labels as to form and information. The bracelet band tube scanners can be obtained from Opticon, Inc. While the invention has been described in connection with the taking of blood samples from hospital patients, it will be readily appreciated that it can be used in connection with other specimen sampling of patients in other environs, such as clinics, physician' offices, sanitariums, or the like. Likewise, the invention can be performed with other forms of machine readable means, such as a magnetically coded bracelet which can be scanned by a magnetic scanner. The invention allows the person who draws the samples to become markedly less involved in the reliability of the sampling.

Since many changes and variations of the disclosed embodiment of the invention may be made without departing from the inventive concept, it is not intended to limit the invention otherwise than as required by the appended claims.

What is claimed is:

1. A portable label printer for printing custom sized labels on site from a continuous label paper tape roll, said printer comprising:
   a) a microprocessor means for receiving and storing a library of label information including label formats, label contents, and label sizes;
   b) scanner means for scanning external machine readable indicia, said scanner means being operably connected to said microprocessor means for enabling said microprocessor means to identify selected label information in said stored library which selected label information comprises label format, label content, and label size, all of which are identified by said scanned external machine readable indicia for each label to be printed;
   c) printing means connected to said microprocessor means, said printing means being operable by said microprocessor means to print, upon command, labels defined by said selected label information;
   d) means for holding said roll of label paper tape;
   e) perforating means connected to said microprocessor means, and operable upon command from said microprocessor means to form rupturable tear lines across the label paper tape at preselected locations dictated by said microprocessor means; and
   f) drive means connected to said microprocessor means, and operable upon command from said microprocessor means to move the label paper tape through said printing means and through said perforating means, to produce a series of labels each being separated from the next by perforated tear lines, which labels may be of the same or different lengths, and which labels have separate selected label information printed thereon.

2. The label printer of claim 1 wherein said scanner means comprises a machine readable indicia scanner means which is operable to identify specific patient identification for said microprocessor means when scanning-patient specific machine readable indicia at a patient's bedside or other patient location.

3. The label printer of claim 2 wherein said scanner means also comprises a medical specimen sample tube scanner means operable to identify medical specimen sample tube types for said microprocessor means responsive to scanning machine readable indicia on specimen sample tubes, and wherein said microprocessor means will signal said printer means to create labels which display tube type information which is specific to the scanned sample tube.

4. The label printer of claim 3 wherein said specimen sample tube scanner means is operable to identify for said microprocessor means medical specimen sample tube sizes upon scanning the sample tubes and wherein said microprocessor means will signal said printing means and said perforating means to create labels in a series thereof, and for use with the same patient which labels are of different sizes and are custom sized to each sample tube scanned.

5. A method of forming a series of adjacent medical patient specimen testing labels from a supply strip of label tape, which adjacent labels are customized for affixation to different specimen carriers; and which adjacent labels display specimen testing instructions for performing different specimen tests, said method comprising the steps of:
   a) providing a source of specimen testing information and specimen tube type information;
   b) providing a supply of said label tape;
   c) printing a series of adjacent labels on said tape, with different specimen testing instructions on at least two of said adjacent labels; and
   d) forming perforated tear lines in said tape between each of the adjacent labels in said series, to form at least two different separable labels in said series.

6. The method of claim 5 wherein said printing step includes the printing of patient information identifying the same patient on said adjacent labels.

7. The method of claim 5 wherein said forming step forms said tear lines at different length intervals along said tape strip to form different size adjacent labels.

8. The method of claim 5 wherein said printing step includes the printing of first bar codes on some of said labels, which first bar codes identify the facility site of the patient; and also the printing of second bar codes on others of said labels, which second bar codes identify an off facility site commercial specimen testing reference laboratory.

9. A method for forming a series of adjacent medical patient specimen testing labels from a supply strip of label tape, which adjacent labels are customized for affixation to different specimen carriers, said method comprising the steps of:
   a) providing a source of specimen testing information and specimen tube type information;
   b) providing a source of patient identification information which is correlated to said testing and tube type information;
   c) printing a series of adjacent labels on said tape, at least two of said adjacent labels having different specimen testing instructions printed thereon, and each of the labels in said series having the same patient identification information printed thereon; and
   d) forming perforated lines in said tape between each of the adjacent labels in said series to form at least two of the adjacent labels with different sizes from each other.

* * * * *